United States Patent
Morrison

(10) Patent No.: US 6,849,609 B2
(45) Date of Patent: Feb. 1, 2005

(54) METHOD AND COMPOSITION FOR CONTROLLED RELEASE ACARBOSE FORMULATIONS

(75) Inventor: James U. Morrison, 3342 N. 5$^{th}$ Ave., Laurel, MS (US) 39440

(73) Assignee: James U. Morrison, Laurel, MS (US)

( * ) Notice: Subject to any disclaimer, the term of this patent is extended or adjusted under 35 U.S.C. 154(b) by 253 days.

(21) Appl. No.: 09/829,707

(22) Filed: Apr. 10, 2001

(65) Prior Publication Data

US 2002/0147159 A1 Oct. 10, 2002

(51) Int. Cl.$^7$ .................... A61K 31/70; A61K 31/715; A01N 25/00
(52) U.S. Cl. .................... 514/42; 514/54; 514/909
(58) Field of Search .................... 514/42, 54, 909

(56) References Cited

U.S. PATENT DOCUMENTS

| | | | |
|---|---|---|---|
| 4,767,850 A | | 8/1988 | Lange et al. |
| 4,904,769 A | | 2/1990 | Rauenbusch |
| 5,643,874 A | * | 7/1997 | Bremer et al. ............. 514/12 |
| 6,130,072 A | | 10/2000 | Beunink et al. |
| 6,309,663 B1 | * | 10/2001 | Patel et al. ............. 424/450 |
| 6,387,361 B1 | * | 5/2002 | Rosner ............. 424/78.01 |

OTHER PUBLICATIONS

Burnham, T.M. and Wickersham, R.M., Acarbose, Drug Facts and Comparisons, 2000, pp., 297–299, Facts and Comparisons, St. Louis, MO.

\* cited by examiner

*Primary Examiner*—James O. Wilson
*Assistant Examiner*—Everett White
(74) *Attorney, Agent, or Firm*—Benesch, Friedlander, Coplan & Aronoff LLP

(57) ABSTRACT

The present invention is directed towards a method and composition for controlled release acarbose formulations. The method and composition disclosed herein combine acarbose and a sustained release matrix. The administration of acarbose alone has been shown to be useful in the treatment of diabetes. Although the initial studies conducted herein were conducted with a delayed release formulation that allowed partial sustained release administered to stimulate sustained release, all indicators from the present invention suggest the formulation of acarbose in a sustained release formulation would have heretofore unexpected benefits. In a sustained release formulation, the ingredient(s) would be a shaped dosage unit having a sustained and regular release of acarbose throughout the small intestine where carbohydrates as a simple sugar are absorbed.

14 Claims, 1 Drawing Sheet

METHOD AND COMPOSITION FOR CONTROLLED RELEASE ACARBOSE FORMULATIONS

BACKGROUND OF THE INVENTION

Acarbose is an inhibitor of the saccharase enzyme complex of the human small intestine and is used in medicine for the treatment of diabetes. Acarbose is chemically O-4,6-didesoxy-4-[(1S,4R,5S,5S)-4,5,6-trihydroxy-3-(hydroxymethyl) -2-cyclohexan-1amino]-α-D-glucopyranosyl-(1→4)-O-α-D-glucopyranosyl((1→4)-D-glucopyranose. The active compound is obtained by fermentation.

U.S. Pat. No. 4,904,769 to Rauenbusch discloses purified acarbose and a method for preparing same using column chromatography.

U.S. Pat. No. 4,767,850 to Lange et al. discloses the purification of acarbose by contacting an acarbose-containing solution with a polymeric cation exchanger.

U.S. Pat. No. 6,130,072 to Beunink et al. relates to a fermentative process for the preparation of acarbose.

Acarbose has been known for some time as an effective agent in the treatment of diabetes mellitus. It is marketed as an orally administered drug under the name Precose® and Glucobay®. Both Precose® and Glucobay® are simply coated with a delayed release coating. Precose® is available in 50 mg and 100 mg round tablets and is currently marketed in the United States by Bayer Corporation (Pharmaceutical Divisions, 400 Morgan Lane, West Haven, Conn. 06516).

SUMMARY OF THE INVENTION

The administration of acarbose alone has been shown to be useful in the treatment of diabetes. Although the initial studies conducted herein were conducted with a delayed release formulation to attain sustained release, all indicators from the present invention suggest the formulation of acarbose in a sustained release formulation would have heretofore unexpected benefits. In a sustained release formulation, the ingredient(s) would be a shaped dosage unit having a sustained and regular release of acarbose throughout the small intestine where carbohydrates as a simple sugar are absorbed.

The term "subject" as used herein means any mammal, including humans. The methods described herein contemplate prophylactic use as well as curative use in therapy for an existing condition.

In one embodiment of the present invention there is provided a method for providing sustained release administration of acarbose or a biological equivalent of thereof. The method allows a relatively constant release of acarbose over a pre-determined amount of time. Importantly, a slow release acarbose formulation provides substantially constant release of acarbose over a pre-determined period of time, thereby ameliorating a supply-demand mismatch involved with the current delayed release administration.

The method of producing the sustained release acarbose formulation, involves the steps of mixing acarbose with a sustained release matrix and compressing the resulting mixture to form tablets. The acarbose comprises about 20%–40% of the weight of the tablet, and ranges from an amount of 25 mg to 300 mg per tablet. Acarbose, a sustained release polymer such as hydroxypropylmethylcellulose (HPMC), and a filler are mixed together. The sustained release acarbose tablet is coated with a glidant, which is selected from the group consisting of colloidal silica, precipitated silica, and mixtures thereof. The sustained release matrix of the tablet is HPMC. The method of producing the sustained release acarbose formulation may also involve coating the tablet with ethyl cellulose.

In another embodiment of the present invention there is provided a composition comprised of acarbose and a sustained release polymeric matrix. Said acarbose may be present in the composition in the amount of 25 mg to 300 mg. Said acarbose in the composition is about 20% to 40% by weight of such composition.

In yet another embodiment of the present invention there is provided a method of treating a patient to stimulate weight loss, such method comprised of administering an acarbose formulation to the patient. The acarbose formulation may be mixed with a delayed release matrix, or alternatively may be mixed with a sustained release matrix.

DESCRIPTION OF THE SPECIFIC EMBODIMENTS

Figure 1:
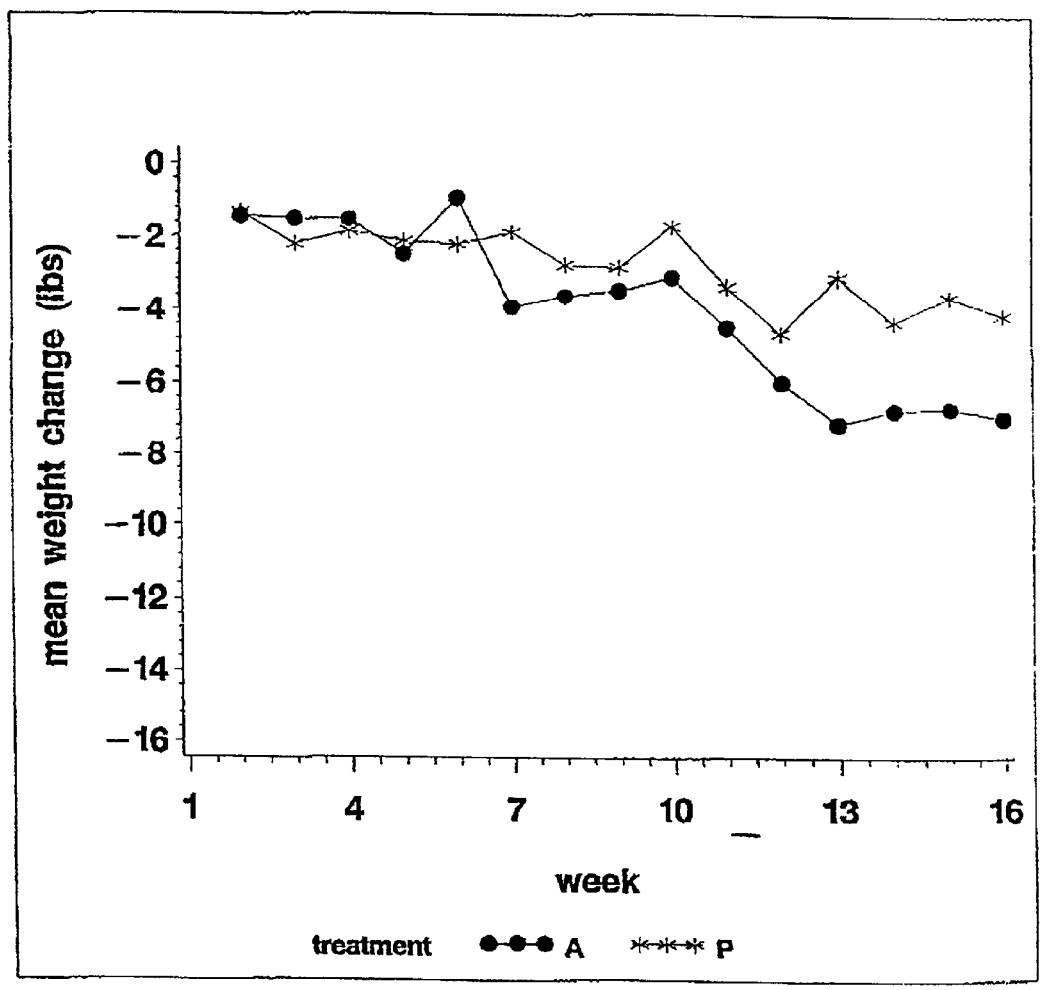
FIG. 1 is a graph illustrating the mean weight change of patients administered delayed release acarbose in accordance with the present invention.

Sustained release products are widely recognized in the art and are of extreme importance in the pharmaceutical field. Through the use of such products, orally and rectally administered medications can be delivered continuously at a substantially uniform rate over a prolonged period of time so as to provide a stable, predetermined concentration of a drug in the small intestine, without requiring close monitoring and frequent re-administration.

Sustained release is achieved by a variety of methods. Two common methods are: 1) providing a sustained release coating upon tablets or microspheres wherein slow release of the active ingredient occurs via either gradual permeation through or gradual breakdown of this coating; or 2) providing a sustained release matrix, such as a fat, a wax, or a polymeric material intermixed with the active ingredient in the tablet itself. These are described for example in "Sustained Action Dosage Forms" *The Theory and Practice of Industrial Pharmacy*, Manford Robinson ch. 14 (L. Lachman et al., eds., 2d ed., 1976) which is incorporated herein by reference thereto.

Sustained release matrix formulations are typically prepared by methods involving pre-granulating the active ingredient together with the matrix material via a wet granulation, solvent granulation, shear-melt or roto-melt granulation, or a wet pre-adsorption technique. In these techniques, a liquid phase is used in order to uniformly mix and/or closely contact the ingredients together so as to provide an evenly distributed matrix in intimate association with the active ingredient. These formation processes help prevent creation of interspersed quick-release zones which would result in discontinuous dissolution of the tablet and thus cause bio-concentration spikes of active ingredient in the patient. They frequently also result in tablets of a relatively higher density than the dry mixed ones, thus allowing the use of tablets, for a given dose, that are smaller than those made by dry mixing for the same intended release rate.

U.S. Pat. No. 4,259,314 to Lowey employs a mixture of cellulose ethers—hydroxypropylmethylcellulose ("HPMC") and hydroxypropyl cellulose—to form a sustained release matrix in which the cellulose ether mixture has a weighted average viscosity rating of 250–4500.

U.S. Pat. No. 5,451,409 to Rencher et al. discloses a dry mixed tablet in which a mixture of hydroxypropyl cellulose and hydroxyethyl cellulose forms the sustained release matrix; 0.5–10% HPMC is also added as a binder.

U.S. Pat. No. 4,369,172; U.S. Pat. No. 4,389,393, & U.S. Pat. No. 4,983,396 to Forest discuss the use of HPMC in a variety of formulations.

Acarbose is an oral alpha glucosidase inhibitor approved for use in the management of non-insulin-dependent diabetes mellitus (NIDDM). Acarbose is complex oligosaccharide that delays the digestion of ingested carbohydrates. It is metabolized exclusively within the gastrointestinal tract, principally by intestinal bacteria, but also by digestive enzymes. It has not been proven that metabolites have inhibitory activity on oligosaccharide digestion.

It is proposed that constant levels of acarbose parent compound throughout the gastrointestinal tract will produce constant inhibitory activity against the digestion of oligosaccharides, thus inhibiting the production of simple sugars. If the utilization of carbohydrates is inhibited, body fat will be used for energy, thus producing weight reduction.

Previous human experience with acarbose has demonstrated a favorable safety profile. Acarbose alone has not been shown to cause hypoglycemia, even when administered to patients in a fasted state. Gastrointestinal symptoms, namely flatulence, diarrhea and abdominal discomfort constitute the most common adverse events experienced by patients taking acarbose. These gastrointestinal symptoms, which have been shown to abate with time, are expected due to the mechanism of action of acarbose.

Humans can utilize only simple sugars. Reduction of complex sugars to simple sugars is a function of the membrane-bound intestinal alpha glucoside hydrolase. This action is inhibited by acarbose. For an agent with this mechanism, if action is to be useful in weight control, a method of keeping the agent in contact with the enteric mucosa over a 24-hour period would be desirable.

The present invention proposes a direct correlation between sustained release acarbose and weight loss. Therapeutic agent(s) may be incorporated in a pill or tablet form or deposited in or coated on the body of a sustained release device (e.g. in a polymeric matrix). The sustained release formulation is preferably comprised of acarbose and/or equivalents thereto. The sustained release formulation may be used with simultaneous or consecutive administration of other active agents. By appropriate choice of the material for the sustained release formulation, a physiologically active amount of acarbose and/or therapeutic mixture may be maintained for an extended period of time (e.g. 4–10 hours) depending on the form of administration and the acceptability of the form. The amount of acarbose or therapeutic mixture has been and will be determined empirically in accordance with known techniques using animal and human models.

Compositions of the present invention may include agents such as a stabilizing compound, which may be administered in any sterile, bio-compatible pharmaceutical carrier, including, but not limited to, saline, buffered saline, dextrose, and water. The compositions may be administered to a patient alone, or in combination with other agents, drugs or hormones. Pharmaceutically-acceptable carriers may also be comprised of excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.) hereby incorporated herein by reference in its entirety. The pharmaceutical composition may be provided as a salt and can be formed with many acids, including but not limited to, hydrochloric, sulfuric, acetic, lactic, tartaric, malic, succinic, etc.

After the controlled release compositions have been prepared, they can be placed in an appropriate container and labeled for treatment of an indicated condition. Such labeling would include amount, frequency, and method of administration.

The exact dosage of the present invention will be determined by the practitioner, in light of factors related to the subject that requires treatment. Dosage and administration are adjusted to provide sufficient levels of the active moiety or to maintain the desired effect with tolerable side effects. Factors which may be taken into account include the severity of the disease state, general health of the subject, age, weight, and gender of the subject, diet, time and frequency of administration, drug combination(s), reaction sensitivities, and tolerance/response to therapy.

The theory and mechanism presented herein are provided solely for the elucidation of the present invention and in no way are meant to limit the scope of the claims.

A sustained release formulation of acarbose (or a biological equivalent thereof) is to be incorporated in a tablet, capsule, or other administration route to achieve the benefits of the present invention. Acarbose in a controlled release formulation in and of itself is an improvement over the state of the art in that it supplies a relatively constant amount of acarbose throughout the bowel. An apparent supply-demand mismatch of acarbose in vivo heightens the need for a slow or controlled acarbose formulation.

The preferred embodiment of the present invention comprises extended-release tablets of an active ingredient which include a sustained release HPMC or ethylcellulose matrix. In a preferred embodiment of the present invention, a combination comprising at least one active ingredient together with hydroxypropylmethylcellulose (HPMC) is mixed and is directly compressed to form tablets. Preferably, the composition is prepared by dry mixing the ingredients. Preferably, one of the active ingredients is acarbose or a pharmacologically acceptable salt thereof. In a preferred embodiment, the amount of active ingredient used is that which is sufficient to produce tablets, each comprising in the range of about 10 mg to 300 mg active ingredient, even more preferably about 100 mg to 250 mg active ingredient, even more preferably about 150 mg to 200 mg active ingredient. A preferred HPMC is Methocel® K100M (produced by The Dow Chemical Co. of Midland, Mich.). Preferably about 20–40% HPMC is used, more preferably about 25–30% and most preferably about 28–29% HPMC.

Glidants, fillers, and other excipients that may be used in the preferred embodiments include those described, e.g., in Handbook of Pharmaceutical Excipients (J. C. Boylan et al., eds., 1986) and in H. A. Lieberman et al., Pharmaceutical Dosage Forms: Tablets (2d ed. 1990). Excipients generally may include: binders and adhesives; disintegrants, and adsorbents; glidants and lubricants; fillers and diluents; and colorants, sweeteners, and flavoring agents. Preferred fillers include calcium salts and simple sugars, for example, calcium phosphates, calcium sulfates, lactose, and mixtures thereof. More preferred fillers include dicalcium phosphate, tribasic calcium phosphate, directly compressible calcium sulfate, anhydrous lactose, flowable lactose (e.g., Fast Flo® lactose produced by Foremost Farms USA of Baraboo, Wis.), and mixtures thereof. Most preferred is dicalcium phosphate ($Ca_2HPO$). Preferably, about 20–40% by weight filler, based on the final weight of the tablets, is employed. However, where the filler consists of one or more sugars alone, preferably about 20–30% of filler is used.

Preferred glidants include colloidal silica and precipitated silica. A preferred colloidal silica is Cab-o-Sil® produced by the Cabot Corp. of Boston, Mass.; a preferred precipitated silica is Syloid® produced by W. R. Grace Co. of New York, N.Y. Preferably, about 0.2–2% by weight of glidant, based on the final weight of the tablets, is employed. Where colloidal silica alone is used, the tablets will preferably comprise about 0.2–0.8% by weight glidant, more preferably about 0.25–0.75%. Preferred lubricants include sodium lauryl sulfate, sodium stearyl fumarate, and metal stearates, alone or in combination with stearic acid. More preferred lubricants include magnesium stearate, zinc stearate, calcium stearate, and mixtures thereof, alone or in combination with stearic acid. Preferably about 0.2–2%, by final weight of the tablets, of lubricant is used, more preferably about 0.25–1.25%. For example, where magnesium stearate is the sole lubricant, the tablets preferably comprise about 0.3–0.5% lubricant; where a magnesium stearate-stearic acid mixture is used as the lubricant, about 0.25% magnesium stearate may be mixed with as much as about 1% stearic acid.

In the preferred embodiment mixing procedure, the active ingredient, e.g., acarbose, sustained release polymer (e.g. HPMC, ethyl cellulose, Kollidon), and the filler, e.g., dicalcium phosphate dihydrate, are passed through a screen into a clean and dry blender, preferably in the order indicated. After mixing for 5 minutes, to the above mixture are added glidants, e.g. colloidal silicate, and this is then passed through a fine mesh screen and into a clean and dry blender. They are mixed for 5–20 minutes, following which a lubricant, e.g., magnesium stearate is screened into the blender and mixed in for an additional 5–15 minutes.

After the foregoing combination has been produced with thorough mixing, it is directly compressed to form tablets, i.e. any solid form, e.g., caplets. These are then coated with a pharmaceutically acceptable coating. Preferred coatings include cellulose ether-based coatings, such as HPMC-based coatings. A preferred coating is Opadry, produced by Colorcon, Inc. of West Point, Pa. Preferably about 0.54% by weight of coating is used (in terms of weight added to the uncoated tablet), more preferably about 1–2%. A wax, e.g., an edible wax such as carnauba wax, may also be applied as a second coating thereover.

Numerous advantages would appear to result from the ability to use acarbose in a sustained release dosage form. These include the use of smaller tablets which are more economical and are easy to administer. The sustained release drug forms of the present invention are expected to be stable and the release rate should not change over an extended storage period. The therapeutic compositions of the present invention, in most cases, will give a steady, reproducible release of the active medicament. The acarbose compositions of the present invention can be formulated to act locally in the lumen or the bowel. The acarbose containing composition can be administered orally to transmit the active ingredients into the gastrointestinal tract. It is to be understood that the present invention is directed generally to an acarbose (or biological equivalent) either alone or in combination in a sustained release formulation and thus is applicable to compressed tablets intended to be swallowed in unit dosage form, and which upon ingestion according to a prescribed regimen give slow and regular release acarbose.

In making up tablets containing an orally administrable active component such as one of the heretofore mentioned, the oral carrier material is thoroughly intermixed with the acarbose and other active ingredients which is also in powdered or granular form or in solution, and any other needed ingredients which are conventional in tablet making such as magnesium stearate, lactose, starch and, in general, binders, fillers, disintegrating agents and the like. The complete mixture, in an amount sufficient to make a uniform batch of tablets, e.g. 50,000, of which each contains an effective amount of active medicament, is then subjected to tableting in conventional tableting machines at compression pressures of 2000 to 16000 lbs/in$^2$ and, because of the use of the specific carrier material of this invention in the production of the tablets, a product is obtained which has the desired hardness, low level of friability and a predetermined prolonged action and a regular delayed release pattern so that the medicament is available over a period of 4 to 10 hours, depending on the precise tablet size, hardness and the particular carrier composition. In this way, it is possible to produce sustained or slow continuous release tablets in relatively simple and economical manner on a commercial scale as contrasted with the more elaborate and more complex materials and procedures heretofore employed or proposed.

The release pattern of active medicament from the carrier of the present invention can be controlled according to the particular medication and its intended therapeutic effect. For orally administered tablets, the rate of release may be 4–10 hours, or as desired. Predetermined release patterns of unusually reliable and constant characteristics can be secured. It has been determined that a rate of release of 6–8 hours is particularly suitable for purposes of the present invention.

The excipient used to control the release of the active ingredient can be a variety of excipients commonly used in control release formulation. The two most common control release excipients are hydroxylproylmethylcellulose ("HPMC") and ethylcellulose. Preferably the tablets formed with these excipients are processed by direct compression, and even more preferably are coated with a control release film. The control release film slows the initial burst of active ingredient. The following illustrative examples are provided for a better understanding of the present invention and are non-limiting. Variations will be obvious to those skilled in the art.

This delivery of sustained-release acarbose to the small intestine will produce maximum inhibition of carbohydrate utilization, resulting in weight control. A study was designed to determine the efficacy and safety of delayed-release acarbose tablets, in conjunction with diet and exercise, as a potential weight-control agent in non-diabetic, healthy, obese patients over a period of 16 weeks. Laboratory data was obtained to monitor systemic side effects, including the changes in levels of serum cholesterol, triglycerides and lipoprotein. Over the 16-week period, patients in Group A received 50 mg. enteric-coated acarbose tablets. All patients received acarbose 25 mg. t.i.d. during a 2-week pretreatment acclimatization phase. All patients underwent a 4-week follow-up phase where they ingested placebo tablets.

Prior to inclusion in the study, relevant baseline information was obtained for all participants. Such baseline information included medical history, physical examination, height and weight, electrocardiogram within two weeks of study initiation, and laboratory analyses.

FIG. 1 illustrates the mean weight change over the course of 16 weeks in participants receiving a delayed release acarbose formulation and those patients receiving a placebo.

As can be seen, those patients receiving the delayed release formulation sustained a weight loss greater than those receiving a placebo. More specifically, of the thirteen subjects that were given an acarbose delayed release formulation, eleven lost weight, with the average weight loss being 7.4 pounds. All indicators from this study would suggest a sustained release formulation would also have benefits such as those described in connection with delayed release formulations.

The invention now being fully described in detail, it will be apparent to one of ordinary skill in the art that many changes and modifications can be made thereto without departing from the spirit or scope of the appended claims. For example it may be beneficial to combine the HPMC with an alkali earth metal to slow the drug release from the tablet (e.g. sodium carbonate or any alkali metal salt of a carboxylic acid). Additionally, new controlled release excipients may be used, such as Rollidon®. Such variations are considered to be within the scope of the invention, which is intended to be limited only to the scope of the claims as interpreted according to the principles of patent law, including the doctrine of equivalents.

Each of the above-referenced U.S. Patents and publications are incorporated in their entirety by reference thereto.

What is claimed is:

1. A chemical composition used to stimulate weight loss in a patient, consisting essentially of:

acarbose; and a sustained release matrix, wherein said acarbose and sustained release matrix are combined to form a mixture.

2. The composition of claim 1, wherein said acarbose is about 20% to about 40% by weight of said composition.

3. The composition of claim 1, wherein said acarbose is present in an amount of about 25 mg to about 300 mg.

4. The composition of claim 1, further consisting essentially of a filler.

5. The composition of claim 4, further consisting essentially of a glidant.

6. The composition of claim 5, further consisting essentially of a lubricant.

7. The composition of claim 6, wherein said lubricant is selected from the group consisting of sodium lauryl sulfate, sodium stearyl fumarate, and metal stearates.

8. The composition of claim 6, wherein said lubricant is selected from the group consisting of magnesium stearate, zinc stearate, calcium stearate, and mixtures thereof.

9. The composition of claim 5, wherein said glidant is selected from the group consisting of colloidal silica and precipitated silica.

10. The composition of claim 1, wherein said sustained release matrix is hydroxypropylmethylcellulose (HPMC).

11. The composition of claim 1, wherein said composition is covered with a coating.

12. The composition of claim 11, wherein said coating is a cellulose ether-based coating.

13. The composition of claim 11, wherein said coating is a cellulose ether-based coating in combination with ethyl cellulose.

14. A method of treating a patient to stimulate weight loss comprising administering a sustained release acarbose formulation to the patient, wherein such formulation does not include a lipase inhibitor.

* * * * *